(12) United States Patent
Kim

(10) Patent No.: US 8,325,876 B2
(45) Date of Patent: Dec. 4, 2012

(54) X-RAY IMAGING APPARATUS

(75) Inventor: Tae Woo Kim, Yongin-si (KR)

(73) Assignees: Vatech Ewoo Holdings, Co., Ltd., Gyeonggi-Do (KR); Rayence Co., Ltd., Gyeonggi-Do (KR)

( * ) Notice: Subject to any disclaimer, the term of this patent is extended or adjusted under 35 U.S.C. 154(b) by 148 days.

(21) Appl. No.: 12/863,180

(22) PCT Filed: Jan. 15, 2009

(86) PCT No.: PCT/KR2009/000233
§ 371 (c)(1),
(2), (4) Date: Jul. 15, 2010

(87) PCT Pub. No.: WO2009/091204
PCT Pub. Date: Jul. 23, 2009

(65) Prior Publication Data
US 2011/0044428 A1  Feb. 24, 2011

(30) Foreign Application Priority Data

Jan. 15, 2008  (KR) .................... 10-2008-0004570

(51) Int. Cl.
*G01N 23/04* (2006.01)
(52) U.S. Cl. ......................................... 378/62
(58) Field of Classification Search .......... 378/167–170, 378/189–191, 98.8, 62
See application file for complete search history.

(56) References Cited

U.S. PATENT DOCUMENTS 7,486,759 B2 * 2/2009 Suzuki et al. .................... 378/4
7,798,708 B2 * 9/2010 Erhardt et al. ................ 378/191

FOREIGN PATENT DOCUMENTS

| JP | 2002-159482 A | 6/2002 |
| JP | 2005-189022 A | 7/2005 |
| KR | 10-1995-0030742 A | 11/1995 |
| KR | 10-2000-0060730 A | 10/2000 |

* cited by examiner

*Primary Examiner* — Irakli Kiknadza
(74) *Attorney, Agent, or Firm* — John K. Park; Park Law Firm

(57) ABSTRACT

The present invention relates to an X-ray imaging apparatus comprising an X-ray source unit generating an X-ray, an X-ray detecting sensor unit having a sensor panel equipped with multiple sensors detecting the X-ray which is generated from the X-ray source unit and passed through an object, and a panel-moving means mounted on the X-ray detecting sensor unit and moving the sensor panel. Thus, employing and butting multiple small X-ray sensors instead of expensive large sensors advantageously reduces the manufacturing cost for the X-ray imaging apparatus, and enables the imaging of the same wide area as with the use of the large sensors.

4 Claims, 3 Drawing Sheets

X-RAY IMAGING APPARATUS

TECHNICAL FIELD

The present invention relates to an X-ray imaging apparatus, and more particularly, the present invention relates to an X-ray imaging apparatus including a source unit, an X-ray sensing unit that includes a sensing panel with a plurality of X-ray sensors, and a unit for moving the sensing panel.

BACKGROUND ART

Generally, in the field of medical diagnosis, an X-ray imaging apparatus transmits a certain amount of X-ray into a part of the human body, and then, an X-ray sensor measures the amount of transmitted X-ray, and measured data are stored in a memory. A computer obtains an X-ray absorption rate on the human body points where the X-ray was transmitted, and then reconstructs it into an image.

The X-ray image apparatus includes an X-ray source and an X-ray detection unit. The X-ray source includes a generator that generates X-ray. The X-ray detection unit includes a sensor that senses X-ray and converts the X-ray into electrical signals.

The bigger the size of the sensor is, the wider the area becomes for which the image is taken.

However, for a big-sized sensor, i.e., a large area sensor, a problem exists concerning the increase of the manufacturing cost, because of a longer manufacturing process.

Therefore, the manufacturing cost increases for X-ray imaging apparatus that includes a large area sensor mentioned above.

SUMMARY OF INVENTION

Technical Problem

The present invention is made to resolve the problem just mentioned above. The object of the present invention is to provide an X-ray imaging apparatus including an X-ray source, an X-ray detection unit that includes a sensing panel with a plurality of X-ray sensors, and a panel moving unit.

Solution to Problem

The X-ray imaging apparatus, according to an embodiment of the present invention, may include an X-ray source that generates X-ray, an X-ray detection unit for detecting X-ray, generated from the X-ray source and transmitted through a target object, wherein the X-ray detection unit includes a sensing panel having a plurality of sensors. This X-ray imaging apparatus also includes a panel moving unit for moving the sensing panel.

In a preferred embodiment, the X-ray imaging apparatus may include: a base that supports an upper structure, a support pillar erected and mounted on the base, an elevating unit installed on the support pillar to move upward and downward, a jaw supporting unit connected to a lower section of the elevating unit, a rotating-arm supporting unit connected to the upper front section of the elevating unit, a rotating-arm supported by the rotating-arm supporting unit and elevated by the elevating unit, wherein the rotating-arm have a X-ray source and an X-ray detection unit, and a rotating-arm driving unit for driving the rotating-arm, wherein the rotating-arm driving unit is located between the rotating-arm and the rotating-arm supporting unit.

In a preferred embodiment, the panel moving unit may move the sensing panel in one of the following directions: upward or downward, to left or to right, or diagonally.

In a preferred embodiment, the panel moving unit may move the sensing panel, so that the X-ray detection unit detects imaging data that has not been obtained because of butting areas.

Advantageous Effects of Invention

In accordance with an X-ray imaging apparatus of the present invention, which includes an X-ray source, an X-ray detection unit including a sensing panel having a plurality of X-ray sensors and a panel moving unit, a plurality number of small area X-ray sensors may be butted in lieu of an expensive large area sensor. Therefore, it is possible to take an image of an area for the same width and length as when using a large area sensor and it is also possible to have the effect of reducing the cost for manufacturing the X-ray imaging apparatus.

| Reference Signs List | |
|---|---|
| 1000: X-ray imaging apparatus | 100: base |
| 200: support pillar | 300: elevating unit |
| 400: jaw supporting unit | 500: rotating-arm supporting unit |
| 600: rotating-arm | 610: X-ray source |
| 620: X-ray detection unit | 621: sensor |
| 622: sensing panel | 623: panel moving unit |
| 624: butting area | |

DESCRIPTION OF EMBODIMENTS

Hereinafter, embodiments of the present invention are explained in detail with the reference to the attached drawings.

Figure 1:
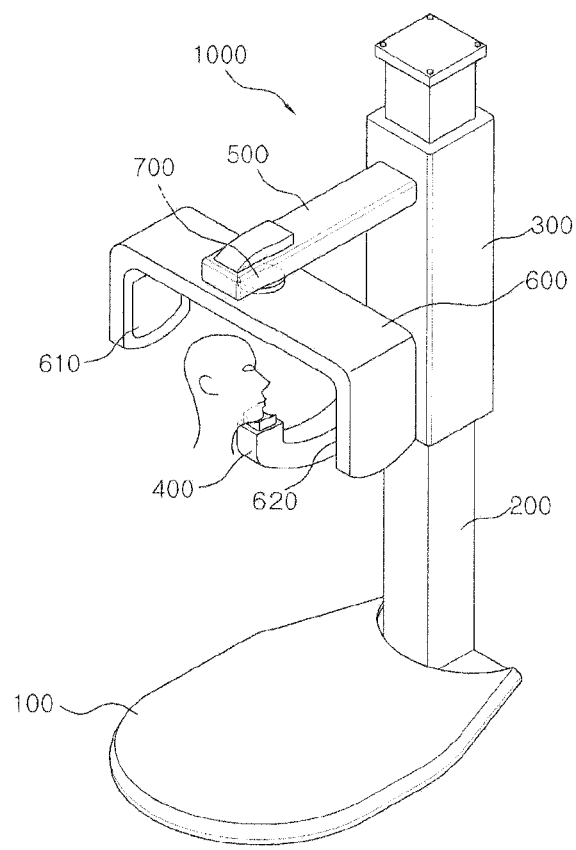
FIG. 1 is a configuration diagram for illustrating an X-ray imaging apparatus, according to an embodiment of the present invention.
Figure 2:
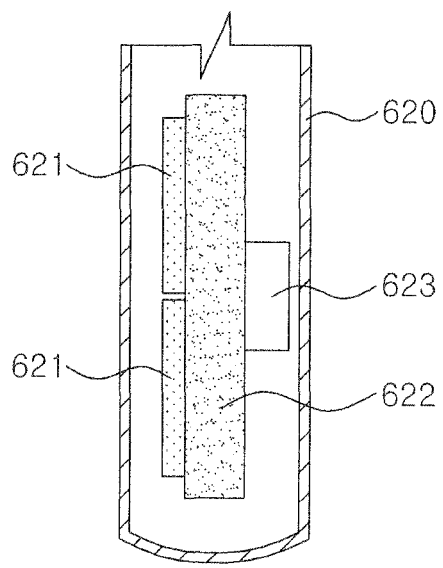
FIG. 2 is a drawing that illustrates an X-ray detection unit in accordance with an embodiment of the present invention.
Figure 3:
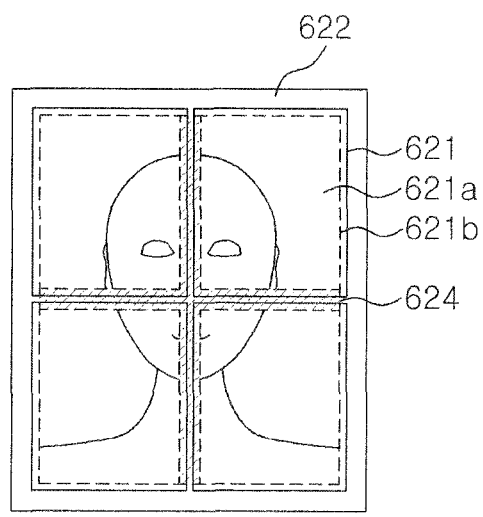
FIG. 3 is a drawing that illustrates a sensing panel in accordance with an embodiment of the present invention.

FIG. 1 is a configuration diagram for illustrating an X-ray imaging apparatus, according to an embodiment of the present invention. FIG. 2 is the drawing that explains an X-ray sensor, according to the embodiment of the present invention. FIG. 3 is a drawing that illustrates a sensing panel, according to an embodiment of the present invention.

Referring to FIG. 1, X-ray imaging apparatus 1000 may include base 100, support pillar 200, elevating unit 300, jaw supporting unit 400, rotating-arm supporting unit 500, rotating-arm 600 and a rotating-arm driving unit.

Base 100 supports support pillar 200 where all the units above are mounted, and support pillar 200 may be erected and installed on one side of the base 100.

Here, in support pillar 200, elevating unit 300 may be installed, where a control motor may be equipped, to change a position either upward or downward, so that the height can be adjusted according to the height of the patient.

Further, jaw supporting unit 400 may be installed at a lower part of elevating unit 300. On jaw supporting unit 400, a jaw of a patient is placed, therefore, allowing the skull of the patient to be placed on X-ray imaging apparatus 1000.

And, rotating-arm supporting unit 500 may be connected to an upper front area of elevating unit 300 in a vertical direction, and rotating-arm supporting unit 500 supports rotating-arm 600 with the rotating-arm driving unit.

Here, rotating-arm 600 may be arranged in a way that X-ray source 610, which generates X-ray, is placed in the opposite direction to X-ray detection unit 620, which detects X-ray generated from X-ray source 610 and transmitted through a target object.

Referring to FIGS. 2 and 3, X-ray detection unit 620 may include sensing panel 622 having a plurality of sensors 621 and panel moving unit 623.

Here, the plurality of sensors 621 may be small area sensors that are sensing the respective X-rays. Sensors 621 may be divided into sensing area 621*a* capable of sensing the respective X-rays and non-sensing area 621*b* not capable of sensing the X-rays as the outer area of sensors 621.

These sensors 621 may be butted against each other, so this way, creating one large area sensor attached to a front section of sensing panel 622. Because of this, the front section of sensing panel 622 may be divided into sensing area 621*a* for each sensor 621 and butting area 624 that is not sensing X-ray because of the gaps generated by butting sensors 621 and non-sensing area (621*b*).

X-ray sensor unit 620 should detect the imaging data by sensing the X-ray covering the entire area comprised of sensing area 621*a* and the butting area 624.

Figure 4:
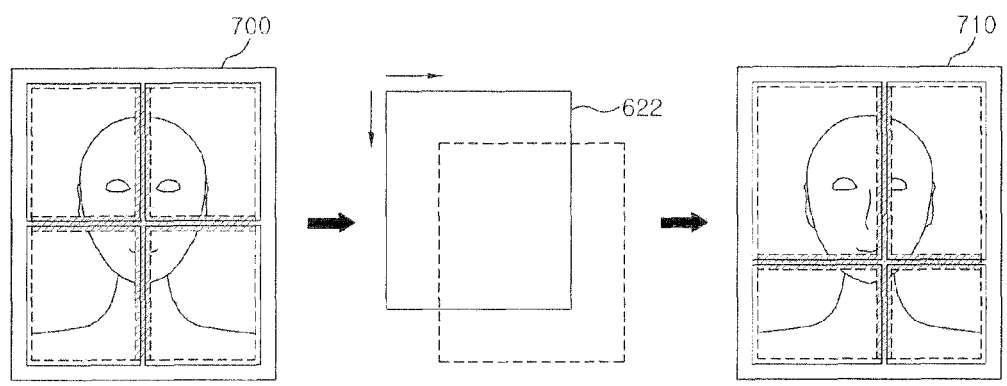
FIG. 4 is a drawing illustrating how to move a sensing unit.

However, as shown in FIG. 4, X-ray sensing unit 620 cannot obtain the complete data because of butting area 624, and therefore, it detects first imaging data 700 except butting area 624. In order to detect the data that was not included in first imaging data 700, the sensing panel 622 may have panel moving unit 623 the back side thereof.

Here, panel moving unit 623 may move sensing panel 622 in one of the following directions of upward or downward, to left or to right, or diagonally, which allows sensor panel 622 to take an X-ray image. This way, X-ray detection unit 620 detects the second imaging data 710 that is not overlapped with butting area 624 in the first imaging data 700.

Figure 5:
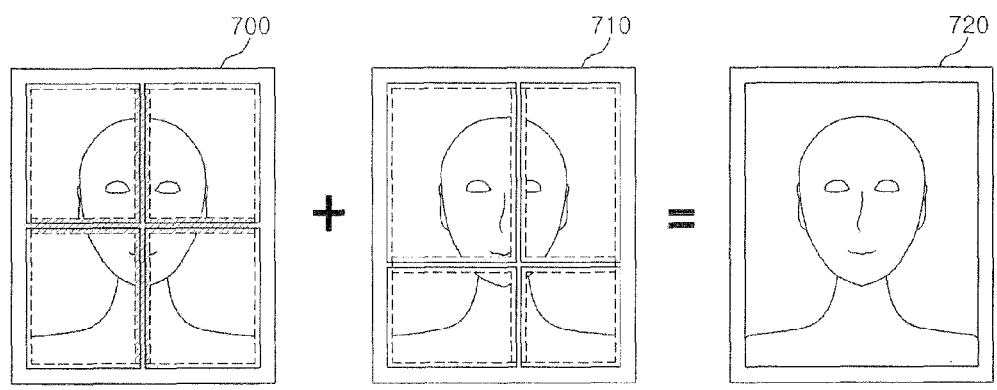
FIG. 5 is a drawing illustrating combining first and second imaging data.

As shown in FIG. 5, the first imaging data 700 and the second imaging data 710 may be combined by a computer, and a complete imaging data 720 may be formed with a correction of the imaging data corresponding to butting area 624 in the first imaging data 700.

Therefore, X-ray imaging apparatus 1000 including all the units described above, can detect complete imaging data by using a plurality of small area sensors 621 in lieu of an expensive, large area sensor. By using the plurality of inexpensive sensors, the manufacturing cost for X-ray imaging apparatus 1000 dramatically decreases.

The configuration and the operation of the present invention are illustrated in the above referring the drawings. The configuration and the operation are merely examples of the present invention. Thus, various changes and modifications may be suggested within the scope of the present invention.

The invention claimed is:

1. An X-ray imaging apparatus comprising:
   an X-ray source generating X-ray;
   an X-ray detection unit for detecting the X-ray generated from the X-ray source and transmitted through a target object, wherein the X-ray detection unit includes a sensing panel having a plurality of sensors; and
   a panel moving unit for moving the sensing panel,
   wherein the plurality of sensors are divided into sensing area and non-sensing area, respectively,
   wherein the sensing panel is divided into sensing area, and butting area which is not sensing X-ray because of the gaps generated by butting the plurality of sensors and the non-sensing area.

2. The X-ray imaging apparatus of claim 1, further comprising:
   a base for supporting an upper structure;
   a support pillar erected and installed on the base;
   an elevating unit installed on the support pillar to move upward and downward;
   a jaw supporting unit connected to a lower section of the elevating unit; a rotating-arm supporting unit connected to the upper front section of the elevating unit;
   a rotating-arm having the X-ray source and the X-ray detection unit, wherein the rotating-arm supported by the rotating-arm supporting unit and elevated by the elevating unit; and
   a rotating-arm driving unit for driving the rotating-arm, wherein the rotating-arm driving unit is located between the rotating-arm and the rotating-arm supporting unit.

3. The X-ray imaging apparatus of claim 2, wherein the panel moving unit moves the sensing panel in one of the following directions: upward or downward, to left or to right, or diagonally.

4. The X-ray imaging apparatus of claim 3, wherein the sensing panel moving unit moves the sensing panel to detect imaging data having not been obtained due to butting areas.

\* \* \* \* \*